US008957234B2

(12) United States Patent
Kolel-Veetil et al.

(10) Patent No.: US 8,957,234 B2
(45) Date of Patent: Feb. 17, 2015

(54) ACETYLENE AND DIACETYLENE COMPOUNDS OF TRANSITION METALS

(71) Applicants: Manoj K. Kolel-Veetil, Alexandria, VA (US); Teddy M. Keller, Fairfax Station, VA (US)

(72) Inventors: Manoj K. Kolel-Veetil, Alexandria, VA (US); Teddy M. Keller, Fairfax Station, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/200,542

(22) Filed: Mar. 7, 2014

(65) Prior Publication Data

US 2014/0274656 A1 Sep. 18, 2014

Related U.S. Application Data

(60) Provisional application No. 61/789,735, filed on Mar. 15, 2013.

(51) Int. Cl.

| | |
|---|---|
| ***C07F 7/28*** | (2006.01) |
| ***B22F 9/18*** | (2006.01) |
| ***C04B 35/56*** | (2006.01) |
| ***C04B 35/58*** | (2006.01) |
| ***C07F 11/00*** | (2006.01) |

(52) U.S. Cl.

CPC ... *C07F 7/28* (2013.01); *B22F 9/18* (2013.01); *C04B 35/5611* (2013.01); *C04B 35/5626* (2013.01); *C04B 35/58007* (2013.01); *C04B 35/58014* (2013.01); *C07F 11/00* (2013.01)

USPC .................................................. 556/52; 556/58

(58) Field of Classification Search

USPC ...................................... 556/52, 58; 423/417

See application file for complete search history.

(56) References Cited

U.S. PATENT DOCUMENTS

2005/0171370 A1* 8/2005 Nishi et al. .................... 556/140
2013/0196132 A1 8/2013 Keller et al.

OTHER PUBLICATIONS

Buschbeck et al., “Homoleptic transition metal acetylides” Coordination Chemistry Reviews 255 (2011) 241-272.

Joswig et al., “The influence of C2 dimers on the stability of TimCn metcar clusters” J. Chem. Phys. 129, 134311 (2008).

Sahoo et al., “Synthesis of Zirconocene-Acetylene and Zirconocene-Diacetylene Polymer” Journal of Polymer Science: Part A: Polymer Chemistry, vol. 37, 3899-3902 (1999).

Zhao et al., “Magic numbers and a growth pathway of high-nuclearity titanium carbide clusters” Solid State Communications 124 (2002) 253-256.

* cited by examiner

*Primary Examiner* — Sudhakar Katakam
*Assistant Examiner* — Pancham Bakshi
(74) *Attorney, Agent, or Firm* — US Naval Research Laboratory; Joesph T. Grunkemeyer

(57) ABSTRACT

A compound having the moiety $M\text{-}[(C{\equiv}C)_n\text{-}M']_m$. Each M and each M' is a transition metal. Each n is 1 or 2, and m is 2 or more. A method of reacting a transition metal halide with 1,2-dilithioacetylene or 1,4-dilithiodiacetylene to form a transition metal compound.

18 Claims, 4 Drawing Sheets

ACETYLENE AND DIACETYLENE COMPOUNDS OF TRANSITION METALS

This application claims the benefit of U.S. Provisional Application No. 61/789,735, filed on Mar. 15, 2013. The provisional application is incorporated herein by reference.

TECHNICAL FIELD

The present disclosure is generally related to compounds containing transition metal (TM) and carbon.

DESCRIPTION OF RELATED ART

Refractory transition metal carbides (TMC) have the highest known melting points (2600-3900° C.) and also outstanding hardness, chemical inertness, wear resistance, electrocatalytic activity, and neutron absorption ability. Refractory TMCs are typically prepared by powder metallurgy methods such as hot press sintering. Alternately, films, fibers, and powders of these ceramics have been made from polymeric precursors, which contain other elements such as oxygen, nitrogen, and hydrogen along with the required TM and carbon. A fundamental exploration of the TM carbide formation process from such polymeric precursors is skewed by the presence of extraneous elements such as oxygen, nitrogen, and hydrogen which imposes additional complexity to the operating chemical transformations. For example, the presence of oxygen in a system containing the TM titanium can preferably result in the formation of $TiO_2$ over TiC. Thus, there is a need for a system that contains only the TM and carbon as its constituents.

Since the late 1960s, there has been an interest in high temperature ceramic materials for such applications as grinding/machining, ball bearings, armors, fibers, and turbine blades. More recently, there has been a resurgence of interest in ultra-high temperature materials for hypersonic vehicles (Mach 5-20) with new propulsion and structural concepts. These vehicles include ballistic missiles, hypersonic cruise missiles, re-entry vehicles, space access vehicles, interceptor missiles, and hypersonic cruise aircraft, which can be easily divided into single-use expendable and reusable systems. These expendable and reusable space vehicles, next generation rocket engines, and hypersonic spacecraft need tough materials and structural components capable of operating at temperatures in excess of 2200° C. and must meet several requirements simultaneously, such as high melting temperature, high strength, and environmental resistance (oxidative resistance). A hypersonic commercial aircraft would be able to travel from New York to Los Angeles in less than an hour. Thus, current increasing interest in hypersonic vehicles and weapons points to the need for new ultra-high temperature materials for wing leading edges and nose tips along with propulsion system components.

Furthermore, there is also current interest in metal carbides with small particle size and high surface area such as tungsten carbide (WC) due to their potential application as catalysts. Selected metal carbides (MCs) such as WC with outstanding catalytic properties similar to Pt promise to be an inexpensive alternative to the expensive noble metals such as Pt and Pd with possibly even superior properties due to their ability to withstand high temperatures and resistance to poisoning, which is common with the noble metals. The anodic chemistry of the direct methanol fuel cell (DMFC) requires the oxidation of methanol and the decomposition of water to produce protons, electrons, and $CO_2$. Strong chemisorption of CO on the noble metals makes these electrocatalysts susceptible to CO poisoning, blocking the active site for methanol oxidation. Consequently, the discovery of less expensive catalysts such as WC, which is more CO tolerant, has helped to commercialize the DMFC.

BRIEF SUMMARY

Disclosed herein is a compound comprising the moiety:

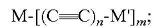

$M\text{-}[(C{\equiv}C)_n\text{-}M']_m$;

Each M and each M' is a transition metal. Each n is 1 or 2, and m is 2 or more.

Also disclosed herein is a method comprising: reacting a transition metal halide with 1,2-dilithioacetylene or 1,4-dilithiodiacetylene to form a transition metal compound.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is the development of transition metal (TM) compounds that may contain only the transition metal and carbon as the component elements that are covalently bonded. Such compounds can function as ideal model systems to study the formation of TM carbides which are an important class of inorganic compounds, along with TM nitrides, with the highest known melting points (2600-3900° C.) and outstanding hardness (9-10 on Mohs hardness scale), chemical inertness, wear resistance, electrocatalytic activity, and neutron absorption ability. They can also function as desirable precursors for forming selective phases of transition metal oxides, nitrides, borides, and silicides by virtue of the specific and prevalent coordination geometry around the respective TM atom. The control of the thermal treatment is also expected to provide control over the selectivity in the facets of the formed nanoparticles. The presence of acetylene groups may facilitate the use of these compounds in various reactions known of acetylenes and diacetylenes such as with organometallic components (for e.g. with $Co_2(CO)_8$), Diels-Alder reactions, click reactions, 1,2- and 1,4-addition polymerization and other addition reactions.

Figure 1:
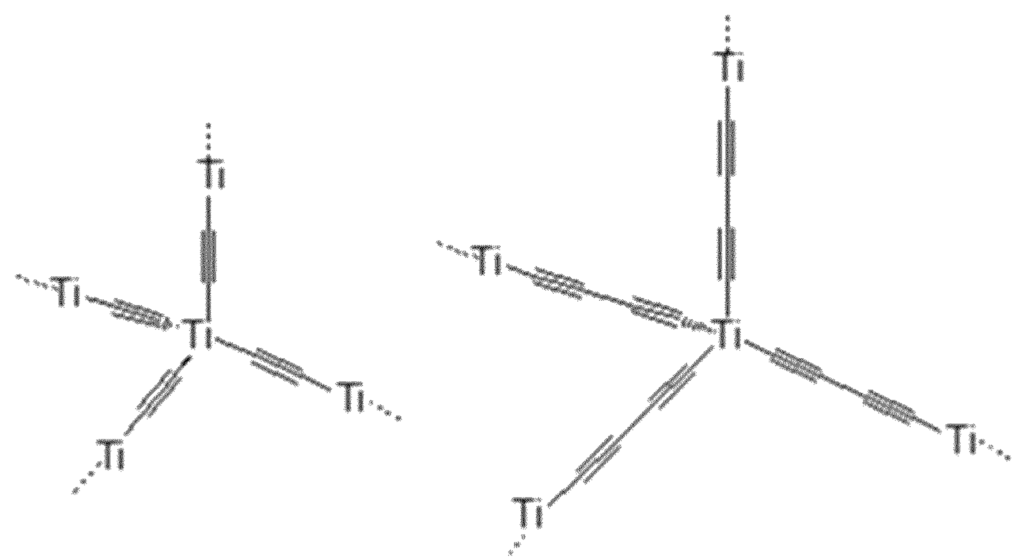
FIG. 1 shows tetrahedral acetylene and diacetylene compounds of titanium.
Figure 2:
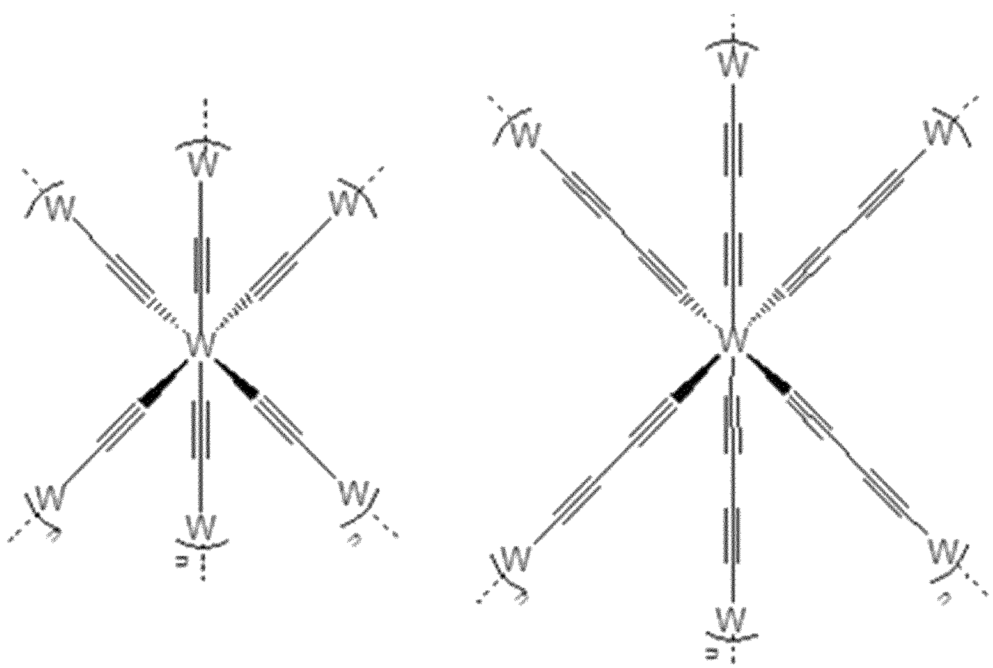
FIG. 2 shows octahedral acetylene and diacetylene compounds of tungsten.

The compounds described herein, depending on the TM precursor, may have fixed coordination geometry around the TM. For example, such compounds derived from a TM halide such as $TiBr_4$ will have the acetylene or diacetylene ligands coordinated in a tetrahedral fashion around the central Ti atom (FIG. 1) or ones formed from $WCl_6$ will have the ligands coordinated in an octahedral fashion around the central W atom (FIG. 2). This feature can lead to the formation of preferred phases of the TM carbide, possibly with further control in the nature of facets of the formed TM carbide nanoparticles. Such complexes can also yield similar selectivity during the formation of TM oxides, nitrides, carbides, or silicides, which make the disclosed group of compounds uniquely valuable. The disclosed TM compounds owing to the connectivity and coordination between the TM and carbon at the molecular level can provide TM carbides, nitrides, borides, oxides or silicides in such small particle sizes (even as low as 1-2 nm in size) upon controlling the reaction dynamics such as the rate of input of thermal energy and/or the temperature of thermal treatment.

The TM acetylene and diacetylene compounds may be synthesized by the reaction between the respective halides of the TM and the dilithiated precursor of acetylene or diacetylene, respectively, as shown below. The latter can be obtained from either trichloroethylene or hexachloro-1,3-butadiene by its reaction with n-BuLi in tetrahydrofuran at temperatures below −75° C. The produced dilithiated precursor in THF is reacted with the respective TM halide in THF by the slow and drop-wise addition of the TM halide solution to the dilithiated reagent below −75° C. (Note: The reaction between the dissolved TM halide and the respective dilithiated reagent is extremely exothermic and has to be conducted under an inert atmosphere below −75° C. with extreme caution. Furthermore, even the dissolution of the TM halide in THF is an exothermic reaction and has to be preferably performed in an inert atmosphere glove box). The reaction is quantitative and proceeds to completion very rapidly. However, typically, the reaction product is left to sit in the reaction vessel for a few hours, prior to work up to collect the final TM-acetylene or -diacetylene product. The work-up involves the transfer of the reaction into a cooled, aqueous, saturated $NH_4Cl$ solution. The resultant mixture is further treated with batches of $Et_2O$ to extract the TM-acetylene or -diacetylene product into the organic layer. Finally, on removal of $Et_2O$, typically, a dark colored product is retrieved.

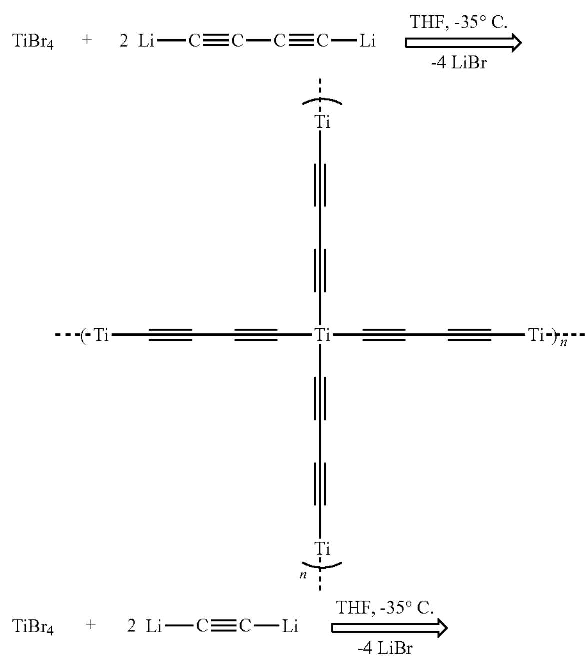

-continued

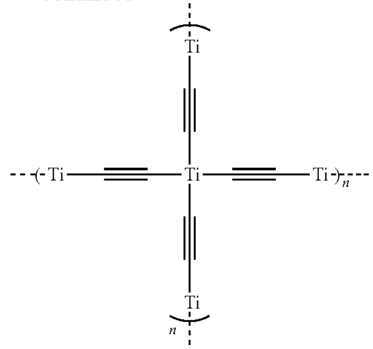

The above formulas show the moiety $M\text{-}[(C{\equiv}C)_n\text{-}M']_m$. As can be seen, the central Ti is M and the four outer Ti atoms are M'. Each of the outer Ti atoms can potential have 1-3 ligands having the formula $—(C{\equiv}C)_n—Ti$. Each of these ligands may themselves have further such ligands, and so on.

It may be possible to form TiC nanoparticles from the presently disclosed compounds by following techniques disclosed in US Patent Appl. Pub. No. 2013/0196132, incorporated herein by reference. Such a conversion may be performed by heating the transition metal compound in an inert atmosphere at a temperature that causes decomposition of the transition metal compound to form transition metal nanoparticles to form a metal nanoparticle composition. This heating may be performed, for example at 150-600° C. The metal nanoparticle composition may be further heated in an inert atmosphere, argon, or nitrogen at a temperature that causes formation of a ceramic comprising nanoparticles of a transition metal carbide or a transition metal nitride in a carbonaceous matrix. This heating may be performed, for example at 500-1900° C. The ceramic may also be heated in an oxygen-containing atmosphere to form an oxide of the transition metal on the surface of the ceramic. TM nitrides may also be formed by heating in nitrogen.

One possible reaction of the TM compounds is hydroboration by reaction with $BH_3$ or $B_2H_6$. Heating under argon may then produce titanium borides and TiC and/or a carbonaceous matrix. Another possible reaction is hydrosilylation by reaction with $Si_3H_8$ or $Si_4H_{10}$. Heating under argon may then produce titanium silicides and a carbonaceous matrix.

The disclosed TM compounds provide model compounds for fundamentally studying the formation of TM carbides in solid state in reactions that only involve the TM and carbon. The examples of such studies so far have involved polymeric systems containing TM, carbon, and other extraneous elements such as oxygen, nitrogen, and hydrogen. Since oxygen and nitrogen have greater affinity for reactions with a TM, the results of such studies from such systems can invariably be impacted and, consequently, skewed.

The preferential kinetic stabilization of a metastable phase such as anatase over its equilibrium phase (rutile) suggests that the particular coordination geometry of the various TM acetylene and diacetylene compounds will yield TM carbides, nitrides, and oxides in preferential phases. This may yield a means to easily produce metastable phases of such compounds.

The presence of only the TM and the acetylene or diacetylene ligands provides a means for functionalizing the acetylene and diacetylene with various catalytically active fragments of well-known TM catalysts which should provide mono-, bi- or multi-metal catalyst systems for various desirable reactions.

The following examples are given to illustrate specific applications. These specific examples are not intended to limit the scope of the disclosure in this application.

EXAMPLE 1

Figure 3:
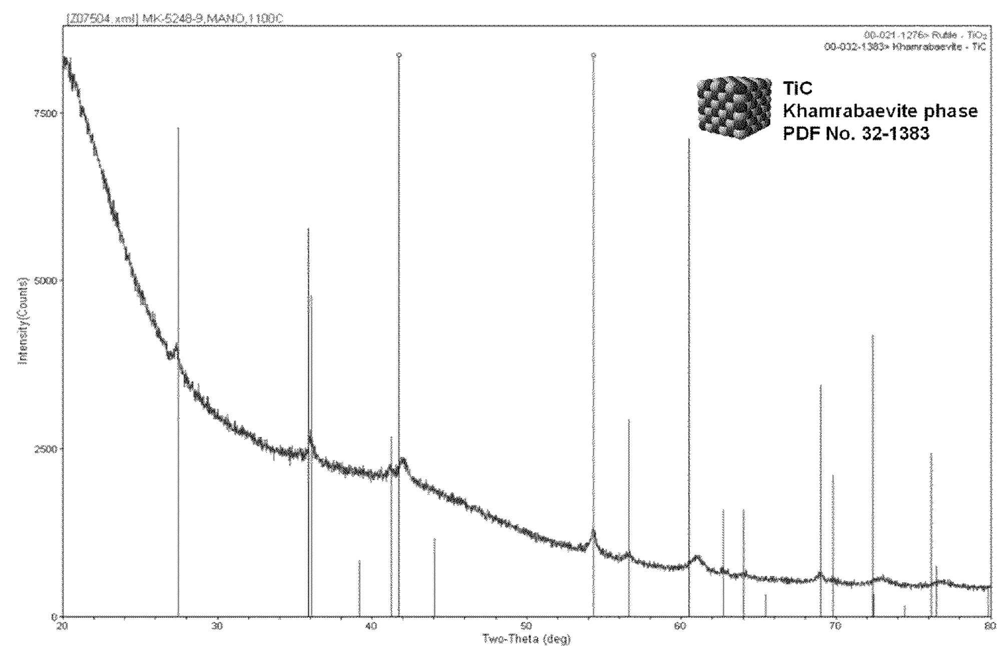
FIG. 3 shows an XRD spectrum of the thermally transformed product from the Ti-acetylene compound treated to 1100° C. in argon.

A sample of the Ti-acetylene compound was pressed into a dime-shaped specimen under vacuum using a pellet maker treated with a mold release agent. The sample was heated in the pellet maker under vacuum to 300° C. for 2 h. After this, a well-formed dime-shaped specimen was released from the pellet maker and was treated in a thermal oven under argon to 1100° C. at the rate of 10° C./min. It was held at this temperature for 1 h and was subsequently cooled to ambient temperature. The resultant product sample contained TiC nanoparticles in a khamrabaevite-like phase (FIG. 3) along with some $TiO_2$ nanoparticles in the rutile phase. The $TiO_2$ nanoparticles are believed to have been formed from the reaction of the initially formed Ti nanoparticles (formed around 800° C. during the thermal treatment) located in the outer surface of the dime-shaped specimen with some contaminant oxygen impurity present in the argon environment. Since the oxygen impurity does not diffuse to the core of the specimen, the interior Ti nanoparticles are afforded an opportunity to react with the carbon matrix and convert to the observed khamrabaevite TiC nanoparticles. Thus, the product is believed to comprise a core comprising TiC nanoparticles and a shell comprising $TiO_2$ nanoparticles.

EXAMPLE 2

Figure 4:
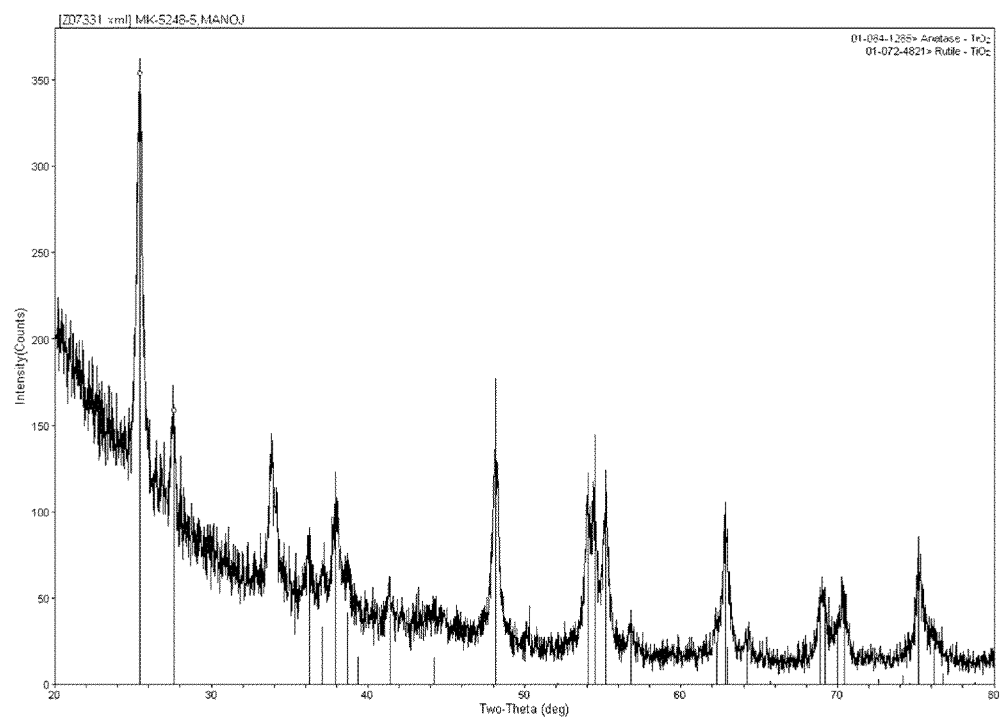
FIG. 4 shows an XRD spectrum of the thermally transformed product from the Ti-acetylene compound treated to 1000° C. in air.

A sample of the Ti-acetylene compound was pressed into a dime-shaped specimen under vacuum using a pellet maker treated with a mold release agent. The sample was heated in the pellet maker under vacuum to 300° C. for 2 h. After this, a well-formed dime-shaped specimen was released from the pellet maker and was treated in a thermal oven under air to 1000° C. at the rate of 10° C./min. It was held at this temperature for 1 h and was subsequently cooled to ambient temperature. The resultant shaped sample contained $TiO_2$ particles of size ~2.4 nm in both anatase and rutile phases as determined by XRD (FIG. 4).

EXAMPLE 3

A sample of the Ti-diacetylene compound was pressed into a dime-shaped specimen under vacuum using a pellet maker treated with a mold release agent. The sample was heated in the pellet maker under vacuum to 300° C. for 2 h. After this, a well-formed dime-shaped specimen was released from the pellet maker and was treated in a thermal oven under argon to 1000° C. at the rate of 10° C./min. It was held at this temperature for 1 h and was subsequently cooled to ambient temperature. The resultant shaped sample contained Ti nanoparticles of ~3 nm in size and $TiO_2$ particles of size ~2.4 nm in rutile phase as determined by XRD.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A compostion comprising the moiety:

$M\text{-}[(C{\equiv}C)_n\text{-}M']_m$;

wherein each M and each M' is a transition metal;
wherein each n is 1 or 2; and
wherein m is 4 or 6.

2. The compostion of claim 1, wherein at least one M' atom has from 1 to m $-(C{\equiv}C)_n$-M' ligands.

3. The compostion of claim 1, wherein the compostion consists essentially of carbon and the transition metal.

4. The compostion of claim 1, wherein M is Ti and m is 4.

5. The compostion of claim 1, wherein M is W, n is 2, and m is 6.

6. A method for making the composition of claim 1, comprising:

reacting a transition metal halide with 1,2-dilithioacetylene or 1,4-dilithiodiacetylene to form a transition metal compound;

wherein the transition metal halide consists of the transition metal and the halide.

7. The method of claim 6, wherein the transition metal halide is $TiBr_4$.

8. The method of claim 6, wherein the transition metal halide is $WCl_6$.

9. The method of claim 6, further comprising:

heating the transition metal compound in an inert atmosphere at a temperature that causes decomposition of the transition metal compound to form transition metal nanoparticles to form a metal nanoparticle composition.

10. The method of claim 9, wherein heating the precursor mixture is performed at 150-600° C.

11. The method of claim 9, further comprising:

heating the metal nanoparticle composition in an inert atmosphere, argon, or nitrogen at a temperature that causes formation of a ceramic comprising nanoparticles of a transition metal carbide or a transition metal nitride in a carbonaceous matrix.

12. The method of claim 11, wherein heating the metal nanoparticle composition is performed at 500-1900° C.

13. The method of claim 11, further comprising: heating the ceramic in an oxygen-containing atmosphere to form an oxide of the transition metal on the surface of the ceramic.

14. The composition of claim 4, wherein M' is Ti.

15. The composition of claim 5, wherein M' is W.

16. The composition of claim 1, wherein the acetylene or diacetylene ligands are coordinated in a tetrahedral or octahedral fashion around the M.

17. The composition of claim 4, wherein the acetylene or diacetylene ligands are coordinated in a tetrahedral fashion around the M.

18. The compound of claim 5, wherein the acetylene or diacetylene ligands are coordinated in a octahedral fashion around the M.

* * * * *